US006699202B1

(12) United States Patent
Gambert et al.

(10) Patent No.: US 6,699,202 B1
(45) Date of Patent: Mar. 2, 2004

(54) METHOD AND DEVICE FOR PHYSIOLOGIC ANALYSIS

(75) Inventors: Rudolf Gambert, Wismar (DE); Peter Schubert, Wismar (DE); Kerstin Wex, Wismar (DE)

(73) Assignee: IT Gambert GmbH (DE)

( * ) Notice: Subject to any disclaimer, the term of this patent is extended or adjusted under 35 U.S.C. 154(b) by 171 days.

(21) Appl. No.: 09/705,654

(22) Filed: Nov. 3, 2000

(51) Int. Cl.$^7$ ................................................. A61B 5/08
(52) U.S. Cl. ...................... 600/532; 600/429; 73/23.3; 422/84; 128/204.22
(58) Field of Search ................................ 600/529, 531, 600/532, 533, 538; 73/23.3; 422/84; 436/900; 482/13; 128/204.22

(56) References Cited

U.S. PATENT DOCUMENTS

| | | | | |
|---|---|---|---|---|
| 3,401,683 A | * | 9/1968 | Webb et al. ................ | 600/531 |
| 4,440,177 A | * | 4/1984 | Anderson et al. ........... | 600/532 |
| 4,463,764 A | * | 8/1984 | Anderson et al. ........... | 600/532 |
| 4,464,926 A | | 8/1984 | Albarda et al. | |
| 4,724,845 A | * | 2/1988 | Callahan .................... | 600/531 |
| 4,995,256 A | | 2/1991 | Norlien et al. | |
| 5,060,656 A | * | 10/1991 | Howard ...................... | 600/531 |
| 5,069,220 A | * | 12/1991 | Casparie et al. ............ | 600/532 |
| 5,072,737 A | * | 12/1991 | Goulding .................... | 600/531 |
| 6,325,978 B1 | * | 12/2001 | Labuda et al. ............... | 422/84 |
| 6,468,222 B1 | * | 10/2002 | Mault et al. ................ | 600/531 |

FOREIGN PATENT DOCUMENTS

| | | |
|---|---|---|
| DE | 37 02 210 | 7/1987 |
| EP | 0692 222 | 1/1996 |

OTHER PUBLICATIONS

Schubert, V., *Messtechnik in der medizinischen Diagnostik*, Medizintechnik, p 68–69, vol. 118 (Feb. 1998).
Sodal, I., *The Medical Mass Spectrometer*, Biomedical Instrumentation & Technology, p. 469–76 (Nov. 1989).
Westenskow, D. and Coleman, D., *Raman Scattering for Respiratory Gas Monitoring in the Operating Room: Advanages, Specifications, and Future Advances*, Biomedical Instrumentation & Technology, p. 485–89.
Merilainen, P., *Sensors for Oxygen Analysis: Paramagnetic, Electrochemical, Polarographic, and Zirconium Oxide Technologies*, Biomedical Instrumentation & Technology, p. 462–66 (Nov. 1989).

* cited by examiner

*Primary Examiner*—Robert L. Nasser
*Assistant Examiner*—Patricia Mallari
(74) *Attorney, Agent, or Firm*—Factor & Partners

(57) ABSTRACT

A new method and a device are disclosed to determine physiologic parameters of a subject by analyzing it's breathing gas with an electrochemical sensor. The measured components of the breathing gas allow for many conclusions about the condition of the subjects's pulmonary system. It is therefore an objective of this invention to determine physiologic parameters from measuring the partial pressure of oxygen in the mainstream of the breathing gas. According to the invention the measurement can be performed non invasive and allows for conclusions about the respiratory and metabolic system of a subject. The invention makes a continuous measurement of the oxygen partial pressure possible, that almost shows no time delay. The invention allows for instance the determination of parameters like the oxygen concentration in the breathing gas, the oxygen consumption of the subject, the heart frequency, the respiratory quotient, the compliance of the pulmonary tract and other physiologic parameters.

13 Claims, 2 Drawing Sheets

METHOD AND DEVICE FOR PHYSIOLOGIC ANALYSIS

BACKGROUND OF THE INVENTION

1. Field of the Invention

This invention generally relates to a new method and a device for the measurement of the oxygen partial pressure in the breath of a human or an animal with an electrochemical sensor and physiologic parameters that can be derived from this.

2. Description of the Prior Art

It has long been known that the analysis of breathing gas can provide much information on the condition of a subject's pulmonary system and other physiologic parameters on a non invasive basis.

A common solution is the timed collection of breathing gas and the concurrent analysis of the collected fractions for volume and constituents. Needless to say, the discontinuity is an inherent drawback since short-interval concentration changes can not be detected with this method. The measurement of breathing gas constituents on a breath-by-breath basis on the other hand gives much more valuable information on various physiologic parameters that otherwise only can be determined with considerable effort or non direct.

Especially the measurement of oxygen in the breathing gas has a high relevance for the determination of various physiological parameters. The measurement of the partial pressure of oxygen in the breathing gas can be performed with different methods, devices and techniques. Merilainen gives a comprehensive survey of the applied technologies in 'Sensors for Oxygen Analysis', Paramagnetic, Electrochemical, Polarographic and Zirconium Oxide Technologies; Biomedical Instrumentation & Technology, 23, 6, 1989.

In the following one should distinguish between side-stream and mainstream measuring techniques. Side-stream techniques principally can be used with all technologies described hereinafter but they are always affected by the disadvantages of the side-stream method. Only spectroscopic and chemiluminescence methods can be performed on a mainstream basis.

In side-stream methods a pump continuously feeds a breath sample through a tubing system into the analyzer unit. Condensing humidity is trapped into a water trap to avoid interferences in the analyzer. In addition to their technical complexity side-stream methods have inherent analytical disadvantages. Caused by the distance that has to be passed through the tubing system and the water trap, the gas concentrations are measured with a time-shift. This time-shift can not be balanced with the necessary accuracy since different gas compositions show different gas viscosities and therefore have different transport times. Another disadvantage of the side-stream method is the mixing of different gas concentrations on the way to the analyzer, so that the measurement gets inaccurate in relation to the actual concentration in the mainstream of the breathing gas.

Methods based on a paramagnetic principle are known (U.S. Pat. No. 4,464,926) and rely on the paramagnetic effect of oxygen. With this different techniques have been described to convert the oxygen partial pressure into an electrical signal. Usually the breathing gas is mixed with a reference gas in a homogeneous magnetic field. By inversion of the magnetic field the pressure difference between the breathing gas and the reference gas can be measured. So far mainstream measurements are impossible due to the size and the weight of the electromagnet that has to be used. Another disadvantage of paramagnetic sensors is their sensitivity to mechanical shock and other paramagnetic substances like nitrous oxides in the breathing gas. Humidity, that can occur due to temperature changes, can also result in considerable problems. For these reasons paramagnetic methods are only applied in a side-stream mode.

Masspectrometry can also be used for fast oxygen measurements, but the employed instrumentation is very complex. In addition the spectrometer is expensive and needs skilled personnel for its operation. Due to their size masspectrometers also can be used only in a side-stream mode. In practice their use is an exception ('The Medical Mass Spectrometer'; Biomedical Instrumentation & Technology, 23, 6, 1989).

Electrochemical sensors based on solid electrolytes are frequently used for oxygen measurements in industrial applications (e.g. the lambda probe in motor vehicles). For many medical applications they show some inherent disadvantages that limit their use or even make it impractical. To achieve the necessary short response time the sensor has to be heated to at least 500 DEG C (U.S. Pat. No. 4,995,256). Thus for reasons of patient safety their use in the mainstream of the breathing gas is impossible. The heating of the sensor also affords a thermal isolation to the exterior and consumes additional electrical power. This limits the miniaturization of the measuring instrument. Anaesthetic gases in the breathing gas can get decomposed at the heated sensor element so that toxic or dangerous substances are generated. In addition anaesthetic gases or their decomposition products can poison the catalytic surface and thereby cause wrong measuring results.

In mainstream methods the components of the breathing gas are directly measured in the volume stream of the breath. This is preferably done right on the breathing tubus or close to the mouth of the subject. Consequently falsifications of the gas concentration or absorption in the tubing system can be avoided. On the other hand the high humidity of the breathing gas at this sampling point sets up higher demands for the measuring technique.

The measurement of carbon dioxide in the mainstream of the breathing gas on a breath-by-breath basis is a common practice since several years due to the development of small and fast carbon dioxide sensors. For this reason a comparable measuring technique for oxygen is very desirable.

Spectroscopic methods make use of the absorption of electromagnetic radiation by the different breathing gases (EP 0692222). Oxygen molecules absorb electromagnetic radiation in accordance to the radiation frequency. To generate the necessary intensity lasers (e.g. as laser diodes) are used. Alternative the raman effect of oxygen can be used ('Raman Scattering in the Operating Room: Advantages, Specifications and Future Advances'; Biomedical Instrumentation & Technology, 23, 6, 1989). Methods that employ laser diodes need a temperature regulation and therefore require sophisticated electronic instrumentation (U.S. Pat No. 5,625,189, U.S. Pat. No. 5,448,071). The application of the raman principle needs a high radiation intensity and therefore also requires complex electronic control units and signal processing. Optical oxygen sensors that operate in the UV range are of minor importance since they show too many cross sensitivities. All spectroscopic methods that can be used for the partial pressure measurement of oxygen are principally sensitive to condensing humidity and other components of the breathing gas. They require sophisticated technical equipment and are used for research especially instead of routine use in clinical practice or at the doctors office. Main disadvantages are high production and maintenance costs as well as the need for skilled personnel for instrument operation. Their high complexity and their large size further limit their use.

Chemiluminescence methods are also used to measure the partial pressure of oxygen (DE 3702210). The method relies on the quenching effect of oxygen on the chemiluminescence of organic compounds that are embedded in a polymer matrix. In principle the method can be miniaturized and could be placed directly in the breathing gas. But there is conflicting information on the toxicity of the aromatic compounds that are used, since they might be introduced into the body during the measurement. In addition the method gives no linear relation between the oxygen partial pressure and the measuring signal. The signal course flattens already at medium partial pressure. Therefore the results get inaccurate at medium and especially at high partial pressures. In addition it is unknown jet, whether common anaesthetic agents like nitrous oxide and halogenated hydrocarbons influence the quenching effect, or cause a swelling of the matrix that leads to inaccurate signals.

It is accordingly a principal object of the present invention to provide a improved method and device to perform oxygen partial pressure measurements in breathing gas on a breath-by-breath basis, while avoiding the shortcomings and drawbacks of the prior art instruments and methods heretofore known.

SUMMARY OF THE INVENTION

It is the object of this invention to provide a simple, cost effective method and device that overcomes the problems referred to above. The method and the device allow the simple but accurate determination of different physiological parameters by the measurement of the partial pressure of oxygen in the mainstream of the breathing gas on a breath-by-breath basis.

According to the invented method to determine components of the breathing gas and thereby physiological parameters, an electrochemical sensor is placed in the mainstream of the breathing gas of a subject and measures the partial pressure of oxygen during one or several breathing cycles almost without time delay. The resulting electric sensor signal which is either directly proportional to the oxygen partial pressure or shows a mathematical relation to the oxygen partial pressure is transmitted to an electronic analyzer.

The course of the oxygen partial pressure can be determined for a part, a complete or several breathing cycles continuously. Upon the measured oxygen partial pressure values different physiologic parameters can be determined.

For instance the inspiratory and expiratory oxygen partial pressure can be determined from the measured oxygen partial pressure values.

The oxygen concentration of the breathing gas can be determined from the measured oxygen partial pressure and the known or measured pressure of the breathing gas.

Besides the expiratory flow can be measured simultaneously with a spirometer in the mainstream of the breathing gas. By integrating and multiplying both expiratory curves, the oxygen uptake of a subject can be calculated.

The metabolic rate and the oxygen consumption can be determined from the oxygen uptake per time.

Additional parameters can be determined from the oxygen consumption and the partial pressure of carbon dioxide or the carbon dioxide concentration, which can be determined in the expiratory breath by mainstream capnography. By applying an additional flow measurement of the breath, the amount of carbon dioxide produced by a subject in a certain time period can be calculated. For instance the respiratory quotient of a subject can be calculated from the oxygen consumption and the produced amount of carbon dioxide by dividing the exhaled carbon dioxide output with the oxygen uptake.

Moreover other gases, for instance oxygen, can be added to the breathing gas. If the subject only breathes oxygen for a certain time and then turns back to breath normal air, other physiologic parameters can be concluded from the signal time characteristics of the expiratory oxygen partial pressure.

The instant invention also allows for the determination of the subject's heart frequency, by analyzing the oxygen partial pressure curve that has been recorded for one or several breathing cycles. The determined heart frequency and oxygen uptake also permit the measurement of the subject's oxygen pulse.

The pattern of the oxygen partial pressure curve can reveal additional pathologic conditions of a subject. The amplitudes of the pulsatory changes in the oxygen partial pressure curve, that are caused by the heart beat during the exhalation, discloses further physiologic parameters.

It is another inventive step of this disclosure, that the breathing frequency can be derived from the time course of the oxygen partial pressure and other pathologic conditions from the breathing pattern. The analysis of the time course of the oxygen partial pressure for one or more breathing cycles allows for the determination of further pulmonary and/or cardiopulmonary parameters.

The device for the determination of physiologic parameters consists of an electrochemical oxygen sensor and an electronic analyzer. The sensor can be operated either in a galvanic or potentiostatic mode. The measurement is performed directly in the mainstream of the breathing gas. The sensors measures the oxygen partial pressure almost without time delay and transmits a signal, that is proportional to the oxygen partial pressure, to the electronic analyzer.

At a sudden change of the oxygen partial pressure the sensor shows a response time of less than 200 milliseconds until it reaches 90% of its end signal. The connected analyzer consists of a processor or a microcontroller and a graphic display.

The instant invention depicts a method and a device that neither show the considerable inaccuracy and time delay that is demonstrated by side stream methods, nor an interference from humidity or anaesthetic agents and the non linear response like optical systems. There is also no risk for the subject from dangerous substances, extreme operating conditions or the emission of electromagnetic radiation. In addition no interference with other measuring instruments can occur.

DETAILED DESCRIPTION OF THE INVENTION

Figure 1:
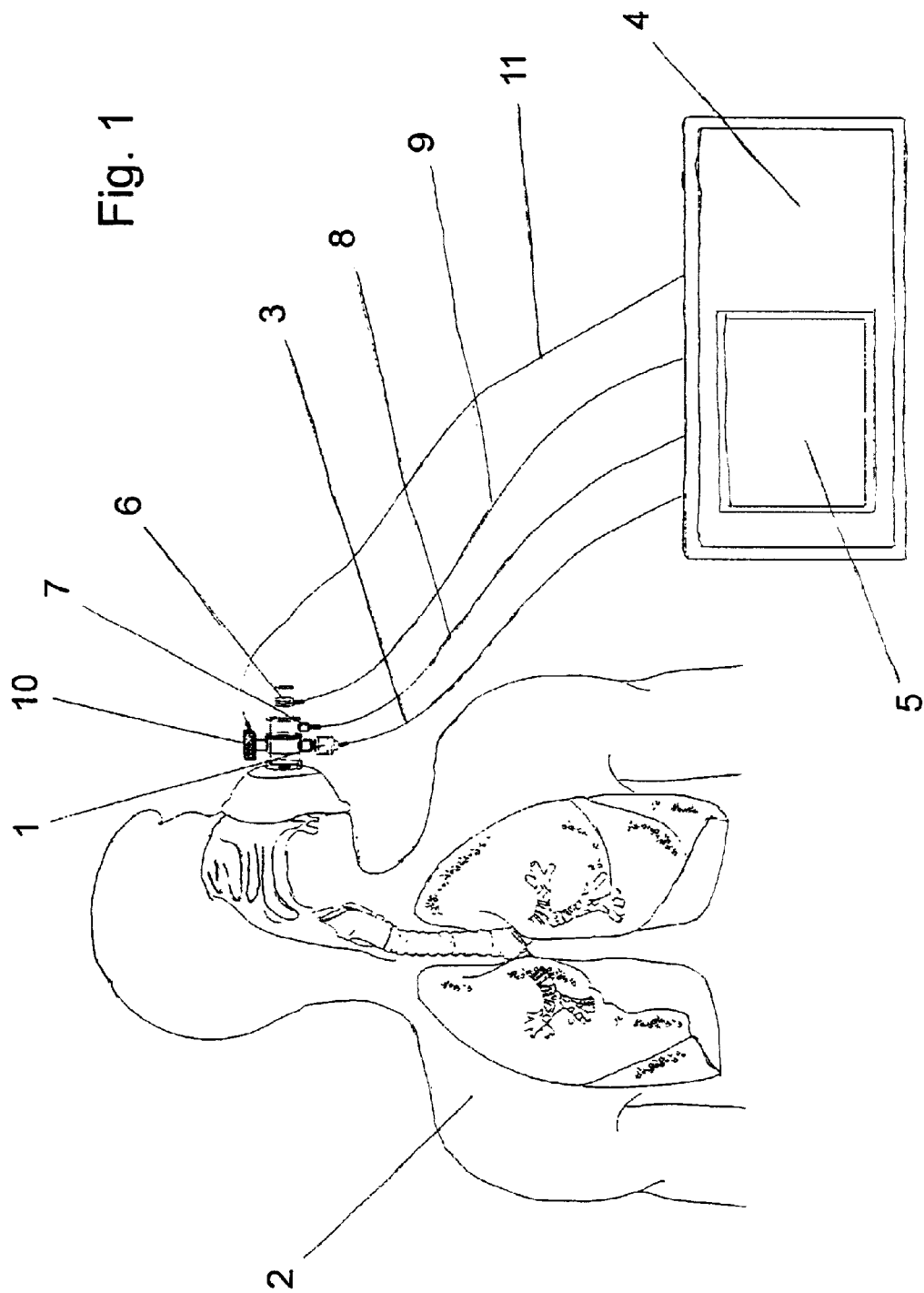
FIG. 1 Device for the determination of physiologic parameters

Referring first to FIG. 1, the electrochemical sensor 1 in the mainstream of the breathing gas, that is either operated potentiostatic or galvanic, produces a signal that is proportional to the oxygen partial pressure almost without time delay. The resulting sensor signals are transmitted to an electronic analyzer, where they are processed and stored. Because of its compact size the electrochemical sensor can be placed directly in the mainstream of the breathing gas. This is also possible, since the sensor is insensitive to humidity, mechanical shock, anaesthetic agents and has only a low power consumption. Electrochemical sensors are much less expensive than other measuring methods and therefore allow a wide-spread application in routine diagnosis and patient monitoring. Galvanic oxygen sensors generally generate an electrical signal, that is directly proportional to the ambient partial pressure of oxygen. The sensor can be calibrated before the measurement is performed. This can be done at normal ambient air and results in a calibration factor. Multiplying this calibration factor with the sensor signal results in the oxygen partial pressure. In case the sensor signal is not directly proportional to the oxygen partial pressure, the oxygen partial pressure can be calculated by using a calibration function.

With this method the course of the oxygen partial pressure can be measured for a part, one or several breathing cycles continuously. Based on the measuring results various physiologic parameters can be determined like the inspiratory and expiratory oxygen partial pressure. Along with the known or measured pressure of the breathing gas, the oxygen concentration of the breathing gas can be determined. Simultaneous measurement of the expiratory flow with a spirometer in the mainstream of the breathing gas gives the oxygen uptake of the subject by integrating and multiplying both expiratory curves metabolic rate and oxygen consumption of a subject can be derived from the oxygen uptake per time. This is of considerable importance since the actual oxygen uptake can vary from oxygen consumption, for instance during blood transfusions. Oxygen consumption and oxygen uptake of a subject are relevant test parameters to analyze the status of patients that had an organ transplantation, cardio-surgery or suffer from a shock.

For the determination of additional parameters, the partial pressure of carbon dioxide or the carbon dioxide concentration can be determined in the expiratory breath by mainstream capnography. Applying a flow measurement of the breath in addition, the amount of carbon dioxide produced by a subject in a certain time period can be calculated. The respiratory quotient of a subject can be calculated from the oxygen consumption and the produced amount of carbon dioxide according to the formula below:

$$Rq = \text{carbon dioxide produced/oxygen uptake} \quad (a)$$

Moreover other gases, for instance oxygen, can be added to the breathing gas. If the subject breathes only oxygen for a certain time period and then turns back to breath normal air, other physiologic parameters can be concluded from the signal time characteristics of the expiratory oxygen partial pressure. The decline in oxygen partial pressure is superimposed by rhythmic pressure changes in the alveoli, that are caused by the heart beat. Counting and standardization on time results in the heart frequency. A more detailed analysis of this pressure changes by considering their amplitude reveals information on the status of a subjects cardio-respiratory system. The determined heart frequency and oxygen uptake give the subject's oxygen pulse.

The pattern of the oxygen partial pressure curve can reveal additional pathologic conditions of a subject. Certain diseases result in characteristic breathing patterns, that can be recognized by the observation of the time course of the breathing profile or the analysis with A, an appropriate software. The geometric form of a breathing curve gives various information on the actual condition of a subject. A flat exhalation curve can reveal diffusion problems in the lower bronchial tract. The amplitude of the pulsatory pressure changes in the exhalation curve, which is caused by the heart beat, discloses further physiologic parameters. The breathing frequency can be derived from the time course of the oxygen partial pressure by counting of the exhalation curves.

FIG. 1 shows a fast oxygen sensor 1 that is placed in the mainstream of the breathing gas of a subject 2. The oxygen sensor 1 gives an analog signal that is directly proportional to the oxygen partial pressure. The signal is transmitted via a cable 3 to an analyzer 4. The analyzer 4 consists of an amplifier, an A/D converter, a microprocessor and a display 5. After amplification and digitalization the signal is multiplied with a calibration factor that has been determined and stored before the measurement by the microprocessor to give the oxygen partial pressure. The actual oxygen partial pressure of the breathing gas is depicted graphically via the microprocessor on the display. The operator can inspect the time course visually.

The microprocessor calculates the breathing frequency from the cycles of the oxygen partial pressure per time. The result can be represented on the display 5. In the mainstream of the breathing gas also a flow sensor 6 and a pressure sensor 7 can be placed. Their signals are transmitted to the analyzer via cables 8 and 9. The actual oxygen uptake of a subject can be calculated from the breathing gas flow and the oxygen concentration by the microprocessor and depicted on the display 5.

In addition a fast carbon dioxide sensor 10 can be placed in the mainstream of the breathing gas. Its signal is transmitted to the analyzer 4 via cable 11. The microprocessor calculates the oxygen consumption and the amount of carbon dioxide produced by a subject from the flow, pressure and the values from both gas sensors 6 and 10 by integrating the area under the curve. The respiratory quotient Rq can be calculated according to formula (a) by the microprocessor and be represented on the display 5 of the analyzer 4.

Figure 2:
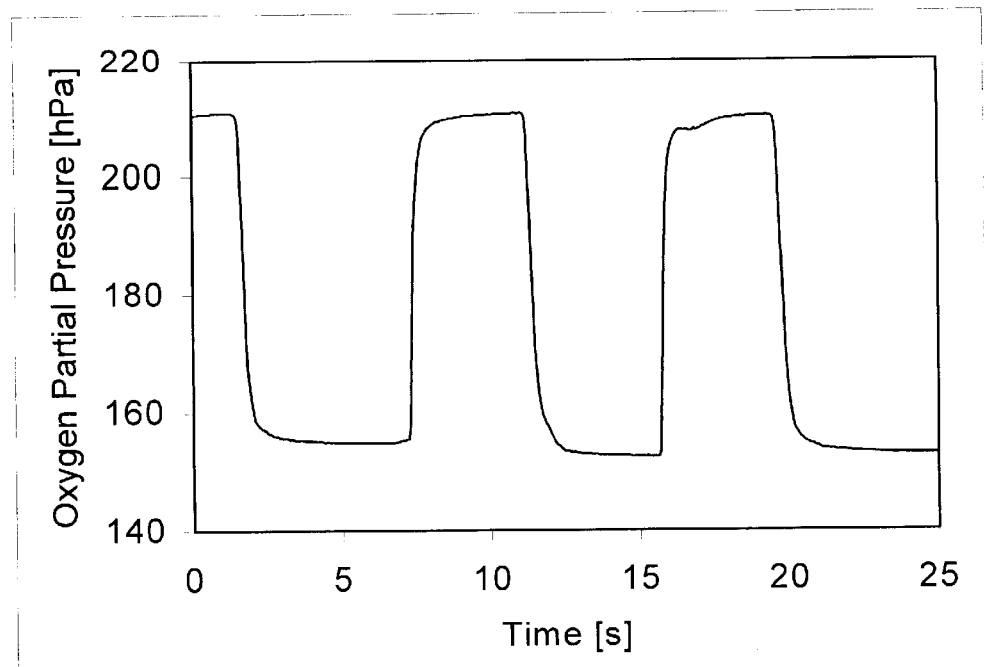
FIG. 2 Graphical representation of a breathing curve

FIG. 2 shows a breathing curve that has been recorded with a fast galvanic oxygen sensor 1 that is placed in the mainstream of the breathing gas of a human being. Plotted is the oxygen partial pressure against time. The inspiratory gas corresponds to approximately 210 hPa oxygen partial pressure or 21 Vol. % oxygen at a total pressure of 1013 hPa. The expiratory oxygen partial pressure amounts to approximately 155 hPa. During the exhalation the oxygen partial pressure declines since more and more breath from lower parts of the bronchial system is exhaled. The plateau in the expiratory phase until the begin of the next inspiration corresponds to the so-called alveolar plateau which represents the oxygen partial pressure in the alveoli.

Figure 3:
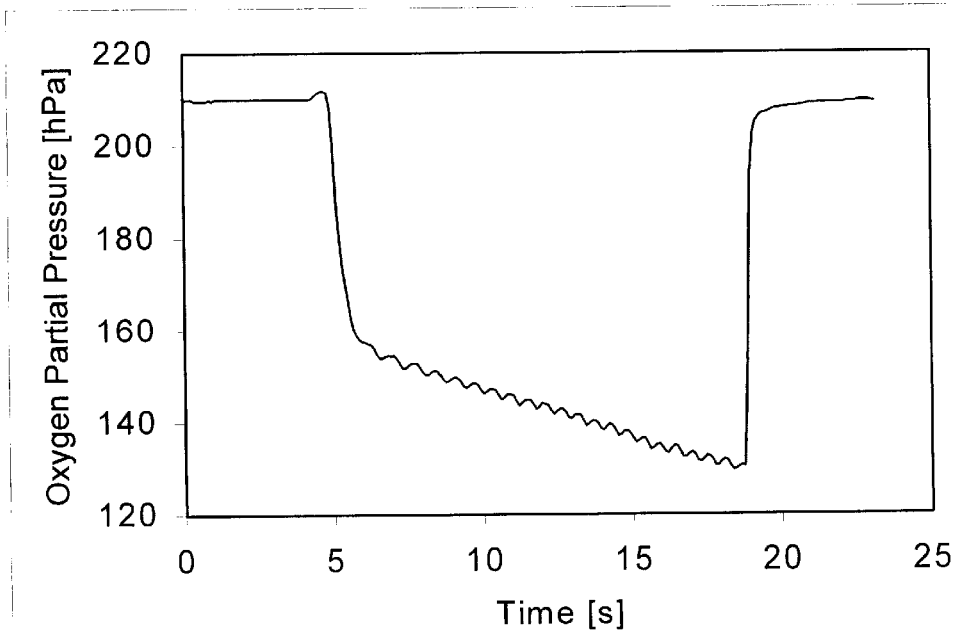
FIG. 3 Graphical representation of an oxygen partial pressure curve of a single breath in higher resolution.

Referring next to FIG. 3 this shows a oxygen partial pressure curve in higher resolution. The microcontroller of the analyzer can calculate the heart frequency of a subject from counting the pulsatory partial pressure changes during the exhalation phase. This can also be depicted on the display of the analyzer.

The microprocessor can save the values in a memory for documentation.

This invention has been described herein in considerable detail in order to comply with the Patent Statutes and to provide those skilled in the art with the information needed to apply the novel principles and to construct and use such specialized components as are required. However, it is to be understood that the invention can be carried out be specifically different equipment and devices, and that various modifications, both as to the equipment details and operating procedures, can be accomplished without departing from the scope of the invention itself.

What is claimed is:

1. A method to determine physiological parameters from a breathing gas of a subject with an electrochemical sensor, the method comprising:

placing an oxygen sensor in a mainstream of the breathing gas that is capable of making one or more measurements of a partial pressure of oxygen during one or several breathing cycles with a response time of less than 200 milliseconds, transmitting an electric sensor signal that is proportional to the oxygen partial pressure or shows a mathematical relation to the oxygen partial pressure to an electronic analyzer, determining an oxygen partial pressure curve from the partial pressure of oxygen as a function of time; and determining a physiologic parameter from the one or more measurements of the partial pressure of oxygen, wherein the step of determining a physiologic parameter comprises the step of determining an inspiratory and an expiratory oxygen partial pressure from the measured oxygen partial pressure values.

2. The method in accordance with claim 1, further comprising the step of determining further pulmonary and/or cardiopulmonary parameters from the analysis of the time course of the oxygen partial pressure curve for one or more breathing cycles.

3. The method in accordance with claim 1, further comprising the step of measuring a pressure of a breathing gas to determine an oxygen concentration of the breathing gas from the measured oxygen partial pressure and the known or measured pressure of the breathing gas.

4. The method in accordance with claim 1, further comprising the step of performing a measurement of expiratory breathing gas flow in addition to a measurement of the expiratory oxygen partial pressure and calculating an oxygen uptake of the subject per time or per ventilated volume.

5. The method in accordance with claim 4, further comprising the step of calculating an oxygen consumption of the subject from the oxygen uptake per time.

6. The method in accordance with claim 5, further comprising the step of determining an amount of expiratory carbon dioxide using another method, and determining metabolic and/or lung function and/or cardiac function parameters from the measured oxygen consumption and expiratory carbon dioxide amount.

7. The method in accordance with claim 1, further comprising the step of adding other gases from the group consisting of oxygen, carbon dioxide, carbon monoxide, helium or nitrogen to the breathing gas for a certain time, so that the subject breathes only the added gas for a certain time, and thereafter,when the subject then turns back to breath normal air, determining at least one of metabolic, lung function, or cardiac function parameters from the signal time characteristics of the expiratory oxygen partial pressure.

8. The method in accordance with claim 1, further comprising the step of determining a heart frequency of the subject by analyzing the oxygen partial pressure curve for one or several breathing cycles.

9. The method in accordance with claim 8, further comprising the step of determining the subject's oxygen uptake by performing a measurement of expiratory breathing gas flow in addition to the measurement of the expiratory oxygen partial pressure and calculating the oxygen uptake of the subject per time or per ventilated volume and determing the subject's oxygen pulse from its heart frequency and its oxygen uptake.

10. The method in accordance with claim 1, further comprising the step of determining at least one of metabolic, lung function and cardiac function parameters of a subject from an amplitude of pulsatory change in the oxygen partial pressure curve.

11. The method in accordance with claim 1, further comprising the step of determining a breathing frequency from the oxygen partial pressure curve.

12. A device for the determination of physiologic parameters consisting of an electrochemical oxygen sensor and an electronic analyzer, such that:

the sensor operates in a galvanic or potentiostatic mode;

a measurement is performed directly in a mainstream of a breathing gas;

the sensor measures an oxygen partial pressure with a response time of less than 200 milliseconds, and transmits a signal that is proportional to the oxygen partial pressure or is related to it by a certain mathematical function to the electronic analyzer.

13. The device according to claim 12, wherein said analyzer includes of a processor or a microcontroller and a graphic display.

* * * * *